(12) United States Patent
Jensen (10) Patent No.: US 12,156,525 B2
(45) Date of Patent: Dec. 3, 2024

(54) SYSTEM AND METHOD FOR HANDLING A BULK FLUID

(71) Applicant: Smarta Industrial Pty Ltd., Cranbourne (AU)

(72) Inventor: Ashley Jensen, Cranbourne (AU)

(73) Assignee: Smarta Industrial Pty Ltd, Cranbourne (AU)

( * ) Notice: Subject to any disclaimer, the term of this patent is extended or adjusted under 35 U.S.C. 154(b) by 1162 days.

(21) Appl. No.: 16/761,043

(22) PCT Filed: Nov. 2, 2018

(86) PCT No.: PCT/AU2018/000214
§ 371 (c)(1),
(2) Date: May 1, 2020

(87) PCT Pub. No.: WO2019/084593
PCT Pub. Date: May 9, 2019

(65) Prior Publication Data
US 2021/0176950 A1    Jun. 17, 2021

(30) Foreign Application Priority Data

Nov. 2, 2017 (AU) ............................... 2017904459
May 10, 2018 (AU) ............................... 2018901608

(51) Int. Cl.
*A23C 3/04* (2006.01)
*A01J 9/04* (2006.01)
(Continued)

(52) U.S. Cl.
CPC ................. *A23C 3/04* (2013.01); *A01J 9/04* (2013.01); *A23L 3/001* (2013.01); *G01K 13/02* (2013.01);
(Continued)

(58) Field of Classification Search
CPC ....... A23C 3/04; A01J 9/04; A01J 9/00; A01J 5/007; A23L 3/001; G01K 13/02; G06Q 10/0832; G01N 33/04
(Continued)

(56) References Cited

U.S. PATENT DOCUMENTS 4,710,755 A    12/1987  Gurney
2003/0146834 A1*   8/2003  Stevens ................... A01J 5/007
                                                              340/521
(Continued)

FOREIGN PATENT DOCUMENTS

WO    1997/005768 A1    2/1997
WO    2018/081849 A1    5/2018

OTHER PUBLICATIONS

Murray Goulburn Co-Operative Co. Ltd, "Supplier Handbook—Southern Milk Region", 2015-2016, 80 pages.
(Continued)

*Primary Examiner* — Minh Q Le
(74) *Attorney, Agent, or Firm* — Chernoff, Vilgauer, McClung & Stenzel, LLP (57) ABSTRACT

A bulk fluid monitoring system and method for monitoring milk is provided, including a plurality of sensors for providing information in relation to properties of a bulk fluid, a memory for holding data parameters including information provided by the sensors and a predetermined time-and-temperature curve for a fluid, a processor for determining whether the information in relation to properties of the bulk fluid is within the bounds of the time and temperature curve for a fluid.

18 Claims, 8 Drawing Sheets

(51) Int. Cl.
*A23L 3/00* (2006.01)
*G01K 13/02* (2021.01)
*G06Q 10/0832* (2023.01)
*A01J 5/007* (2006.01)
*A01J 9/00* (2006.01)
*G01N 33/04* (2006.01)

(52) U.S. Cl.
CPC ........... *G06Q 10/0832* (2013.01); *A01J 5/007* (2013.01); *A01J 9/00* (2013.01); *G01N 33/04* (2013.01)

(58) Field of Classification Search
USPC .............................................. 137/551, 487.5
See application file for complete search history.

(56) References Cited

U.S. PATENT DOCUMENTS

| | | | | |
|---|---|---|---|---|
| 2004/0025606 | A1* | 2/2004 | Veenstra | A01J 7/027 119/14.08 |
| 2007/0017448 | A1 | 1/2007 | Stevens et al. | |
| 2008/0109266 | A1* | 5/2008 | Bjork | G06Q 10/063 119/14.08 |
| 2015/0313172 | A1* | 11/2015 | Johnston | A01J 5/007 119/14.14 |
| 2016/0371642 | A1* | 12/2016 | Wilkinson | G06Q 10/0832 |
| 2017/0099801 | A1* | 4/2017 | Van Tilburg | A01J 7/022 |
| 2017/0150695 | A1* | 6/2017 | Meillan | A01J 5/01 |
| 2019/0049926 | A1* | 2/2019 | Beasley | G06K 19/0717 |
| 2019/0205835 | A1* | 7/2019 | Chopko | G06Q 10/08 |
| 2020/0311664 | A1* | 10/2020 | Poolman | G06Q 10/08 |
| 2020/0323245 | A1* | 10/2020 | Le | B65D 81/18 |
| 2021/0150467 | A1* | 5/2021 | Sakai | F25D 29/003 |
| 2021/0245578 | A1* | 8/2021 | N | G06Q 10/20 |
| 2021/0279676 | A1* | 9/2021 | Poolman | G06Q 10/087 |

OTHER PUBLICATIONS

International Search Report prepared by the Australian Patent Office for PCT/AU2018/000214, Feb. 27, 2019, 4 pages.

Written Opinion prepared by the Australian Patent Office for PCT/AU2018/000214, Feb. 27, 2019, 10 pages.

* cited by examiner

| Flow Meter Make | Flow Meter Model | Max Flow Rate (L/min) | Min Flow Rate (L/min) | Min Qty (L) |
|---|---|---|---|---|
| Process Data ™ | PD340-C25 | 116 | 16 | 5 |
| Process Data ™ | PD340-C38 | 333 | 33 | 10 |
| Process Data ™ | PD340-C51 | 666 | 66 | 50 |
| Process Data ™ | PD340-C63 | 1333 | 83 | 50 |
| Process Data ™ | PD340-C76 | 2000 | 200 | 100 |
| Process Data ™ | PD340-C102 | 3332 | 300 | 100 |
| Diessel ™ | IZM-E DN 50 G2 | 700 | 70 | 200 |
| Diessel ™ | IZM-E DN 65 G2 | 1000 | 100 | 500 |
| Diessel ™ | IZM-E DN 80 G2 | 1500 | 150 | 500 |
| Diessel ™ | IZM-E DN 100 | 4500 | 900 | 500 |
| Diessel ™ | IZM-SEG2 DN 50 | 700 | 70 | 200 |
| Diessel ™ | IZM-SEG2 DN 65 | 1000 | 100 | 500 |
| Diessel ™ | IZM-SEG2 DN 80 | 1500 | 150 | 500 |
| Diessel ™ | IZM-SEG2 DN 100 | 4500 | 900 | 500 |
| DME ™ | MIF C63 | 1000 | 100 | 500 |
| DME ™ | MIF C76 | 1500 | 150 | 500 |
| DME ™ | MIF C63/PD340 | 1000 | 100 | 500 |
| DME ™ | MIF C76/PD340 | 1500 | 150 | 500 |
| GEA ™ | IZMAG DN 80 | 3000 | 60 | 200 |

Figure 8

SYSTEM AND METHOD FOR HANDLING A BULK FLUID

FIELD OF INVENTION

This invention relates to a system and method for monitoring the characteristics of a bulk fluid. More particularly, this invention relates to a system and method for monitoring characteristics such as temperature of milk and determining compliance with standards.

BACKGROUND ART

The following references to and descriptions of prior proposals or products are not intended to be, and are not to be construed as, statements or admissions of common general knowledge in the art. In particular, the following prior art discussion should not be assumed to relate to what is commonly or well known by the person skilled in the art, but to assist in the inventive process undertaken by the inventor(s) and in the understanding of the invention.

Ensuring the quality of products intended for human consumption is important not only for safety but also to ensure the suppliers obtain the best price for their product. In the case of bulk fluids such as milk, suppliers such as dairies collect milk from a number of animals, store it in bulk in a vat, where it is then transported to manufacturers.

There are a number of standards for handling raw milk collected at dairies, specifically relating to temperature and milking times. For example, European requirements are that milk must be cooled immediately, within 2 hours from completion of milking, to no more than 8° C. in the case of daily collection, and 6° C. in the case where milk is not collected daily. Food Standards Australia and New Zealand (FSANZ) guidelines for raw milk collection advise that milk should be cooled on farm collection to 5° C. within 3.5 hours from the start of milking. This is more stringent than the European standards, and also requires measurement of different parameters, namely the time milking starts, rather than the time milking stops. Failure to comply with either or both of the standards can result in the milk and subsequent products being of unacceptable quality and/or unable to be sold.

In one simple scenario, milk from one milking of a herd of dairy cows is collected into a vat, where the milk is typically around 37° C. The milk is then cooled to below the required temperature. Once fully cooled, the milk may be picked up by tanker lorry or truck for delivery to a processing installation for packaging or transforming into other products, such as homogenised milk, reduced-fat milk, yoghurt and cream. Typically, the milk temperature is measured just prior to transfer from the vat to the delivery truck to ensure compliance. An object of the present invention is to ameliorate the aforementioned disadvantages of the prior art or to at least provide a useful alternative thereto.

STATEMENT OF INVENTION

The invention according to one or more aspects is as defined in the independent claims. The claims may include features additional to the invention, or may exclude in the initial documents filed features that are ultimately used to characterise the invention. Some optional and/or preferred features of the invention are defined in the dependent claims.

Accordingly, in one aspect of the invention there is provided:

A bulk fluid monitoring system including:
 one or more sensors providing data in relation to a plurality of properties of a bulk volume of a fluid;
 a memory for holding:
  a set of data parameters;
  the data provided by the sensors; and
  a predetermined time-and-temperature requirement for the fluid corresponding to the set of data parameters that comply by falling on or within ranges of values either side of a standard time and temperature curve for the fluid;
 a processor; and
 an output;
wherein the processor:
 processes the sensor data to generate sensor information;
 compares the sensor information with the set of data parameters to generate a compliance value; and
 sends a signal to the output to generate an indicator of non-compliance where the compliance value corresponds to the fluid being outside the set of data parameters.

The system may provide the advantage of determining whether the bulk fluid has been handled correctly, without requiring manual input at the time and point of collection.

Specifically, by monitoring the set of parameters including one or more parameters of the bulk fluid according to a standard set of parameters, not only can a record of the handling of the fluid be created by the processor and generated as a compliance information report, but compliance information and features about collection of the fluid can be determined independent of manual input. Such compliance information can be collated, for example by the processor. The compliance information may be sent to a remote information processing device or installation for monitoring and logistics applications. The compliance information may be used to coordinate the collection of the fluid from a plurality of collection points and transport to one or more destinations.

The one or more sensors may include a plurality of sensors. The sensors preferably include a sensor for measuring the temperature of a bulk fluid and a sensor for measuring a change in the volume of the bulk fluid. The measurement of a change in the volume of the bulk fluid may provide an advantage that the time that collection of the fluid is started or the time of completion of collection of the bulk fluid can be determined. This measurement can be made independent of, or without, manual input regarding collection start and finish times.

Manual input might involve an operator actively taking a temperature measurement when the operator considers it timely to do so. Reliance in the prior art is on the operator timeously and accurately making the measurements, noting that compliance, consistency and accuracy have been reliant on individual operators.

The system's memory may store for information in relation to at least one set of standards for temperature and time parameters for a bulk fluid. This provides the advantage of allowing the temperature of the bulk fluid to be compared to one or a number of standards.

The output may provide information in relation to one or more of:
 a data logging device;
 a communication network to transmit information to a remote location; and
 an indicator.

The indicator preferably is adapted to provide an audible or visual signal associated with the indicator of non-compliance. The indicator may include a visual or audible indication of whether the properties of the bulk fluid being monitored are within one of, or a plurality of, the standards for temperature parameters stored on the device.

The fluid is preferably a liquid. The fluid may be temperature sensitive. The fluid may degrade, denature or become unstable beyond a predetermined temperature range. The predetermined range may correspond to a particular cooling envelope. This may define higher and lower acceptable temperatures for a fluid at a particular time in a time line describing permissible temperatures for the fluid over a period of time. The fluid may be a food product. The fluid may be milk. The milk may be liquid milked immediately prior to collection as a bulk volume of milk.

The time and temperature curve for the fluid may include one or more milk cooling curves. One or more cooling curve standards may be stored in the memory of the monitoring system. The one or more stored cooling curve standards may be compared to the measured values of temperature and volume of the milk. The measurements may be progressively recorded as the fluid is collected and delivered to a fluid container, such as a vat or fluid transport tanker, including a milk tanker. The measurements are preferably taken of the fluid in the container as the volume of the fluid in the container changes.

Typically, the fluid is first collected in a bulk storage installation at the site of collection. For example, milk may be extracted from a plurality of cow and delivered to a milk vat. The bulk fluid monitoring system monitors the milk as it is delivered to a vat, measuring the temperature of the fluid and the change in volume. The change in volume enables the detection of the start, the filling period and the finishing time of the milking period, to provide the data required for the cooling curve for the fluid.

The memory may be in the form of a data storage device. The cooling curve of the fluid may be logged and stored in the memory. This may provide a full history of the temperature of the fluid from initial collection in a bulk fluid storage container, to transfer to a tanker transport for delivery.

In another aspect of the invention described above, the invention provides a method of utilising the bulk fluid monitoring system to monitor a bulk fluid in a storage container, as the fluid is collected from one or more local sources and transferred to the container, the method including the steps of:
  receiving and storing data or information regarding desired properties of a particular type of fluid;
  monitoring the properties of a changing volume of the fluid corresponding to the particular type of fluid in a storage container;
  determining time based measurable properties of the fluid over time and storing those time based properties;
  comparing the time based properties of the fluid to the stored information of the fluid; and
  outputting the result of the comparison.

In another aspect of the invention described above, the invention provides a method of utilising the bulk fluid monitoring system to monitor a bulk fluid in a storage container, the fluid being a particular type of fluid, as the fluid is collected from one or more local sources and transferred to the container, the method including the steps of:
  storing information regarding desired properties of the fluid or a broad curve delineating a range of acceptable values of one or more properties of the particular type of the fluid over time;
  receiving and monitoring the properties of a changing volume of the bulk fluid corresponding to the particular type of fluid in a storage container;
  determining time based properties of the changing volume of the fluid;
  comparing the time based properties of the fluid to the stored information of the fluid; and
  generating an output indicating the result of the comparison being that the time based properties fall within or outside the range delineated by the stored information.

The step of receiving and storing information regarding desired properties of the fluid includes receiving information in relation to temperature of the fluid over time and/or relative to the volume of the fluid in the bulk fluid storage container.

The method of monitoring a bulk fluid may include calculating the sensor information with regard to the start time and/or the end time of the fluid entering the storage container based on volume information. The method may further include calculating the sensor information with regard to the start time and/or the end time of the fluid entering the storage container based on the temperature information of the fluid.

In another optional feature of the invention, there is provided a tanker metering control system comprising a vat monitoring device comprising:
  sensors measuring at least one property of a bulk fluid;
  a data storage device for storing at least one standard comprising a set of parameters
  in relation to the property measured over time; and
  an output device,
control system adapted to:
  compare the measured property with the standard;
  determine if the property measured over time complies with the standard; and
  generate a fluid volume, viability and readiness indicator in the output device.

The bulk fluid monitoring system preferably includes a tanker metering controller installed or mounted on a tanker vehicle. The controller is preferably in communication with the monitoring device associated with the vat that is adapted to receive a bulk food fluid. The bulk fluid characteristically has time critical properties that are vital to food safety. Typically, the time critical property is temperature over time. For the monitoring of the bulk fluid, the vat includes the sensors measuring at least the temperature of the bulk fluid over time. The tanker vehicle may also have sensors for measuring at least the temperature of the bulk fluid contained in the vehicle tank over time. This may be achieved by taking periodic measurements of the property of the bulk fluid. These data measurements may be collected by the controller. Advantageously, a remote server may process the data or information from the monitoring device and the controller to determine an optimal driving route of the tanker vehicle, and pickup and delivery times.

The tank monitoring device may be in communication with the processor. The processor may include a data storage device that stores at least one standard set of property over time parameters in relation to the property measured over time. The processor has an out put device. The processor also generates output information including the location of the vehicle at periodic intervals.

The monitoring system may be adapted to:
compare the measured property with the standard;
determine if the property measured over time complies with the standard; and
generate a fluid volume, viability and readiness indicator in the output device.

The tanker metering control system is preferably linked to a tanker route control system. The fluid volume, viability and readiness indicator may be used to prepare a transport schedule. Multiple fluid volume, viability and readiness indicators each generated by a plurality of tanker metering control systems in spaced locations may be used to prepare a transport schedule.

The transport schedule may determine an optimal route for at least one tanker. The transport schedule or optimal route may be communicated to a remote smart or navigation device. The smart and/or navigation device may be used by a driver or navigator to determine the transport route to be followed to pick up deliveries of the bulk fluid, according to the fluid volume, viability and readiness indicator at each location. Preferably, each vat monitoring device at each spaced location captures the level and temperature of a bulk fluid contained in each vat at each location.

The tanker metering control system is preferably adapted to control the tanker pickups. The tanker metering control system may measure and capture, as an output to the output device, information regarding the amount loaded and the temperature of an amount of bulk fluid retrieved at a location.

The tanker metering control system may be used for route planning and route optimisation of a tanker transport utilising the indicator information generated by the tanker metering control system.

According to the invention, vat monitoring advantageously allows the monitoring system to determine how much milk is at a particular location (such as a dairy farm), what the temperature of the bulk fluid currently is in the vat, and the expected time that the fluid, according to the fluid volume, viability and readiness indicator, will be ready for pick up by the tanker. In the context of the fluid being milk, the monitoring system may be used to determine when the milk contained in the vat will be cooled to the right temperature ready to be picked up.

The tanker metering control system may be supplied with real-time information on what tankers are available with the system, what their capacity is, and what fluid capacity is according to their configuration, eg. with reference to compartment sizes.

BRIEF DESCRIPTION OF THE DRAWINGS

The invention may be better understood from the following non-limiting description of preferred embodiments, in which.

DETAILED DESCRIPTION OF THE DRAWINGS

Preferred features of the present invention will now be described with particular reference to the accompanying drawings. However, it is to be understood that the features illustrated in and described with reference to the drawings are not to be construed as limiting on the scope of the invention.

Figure 1:
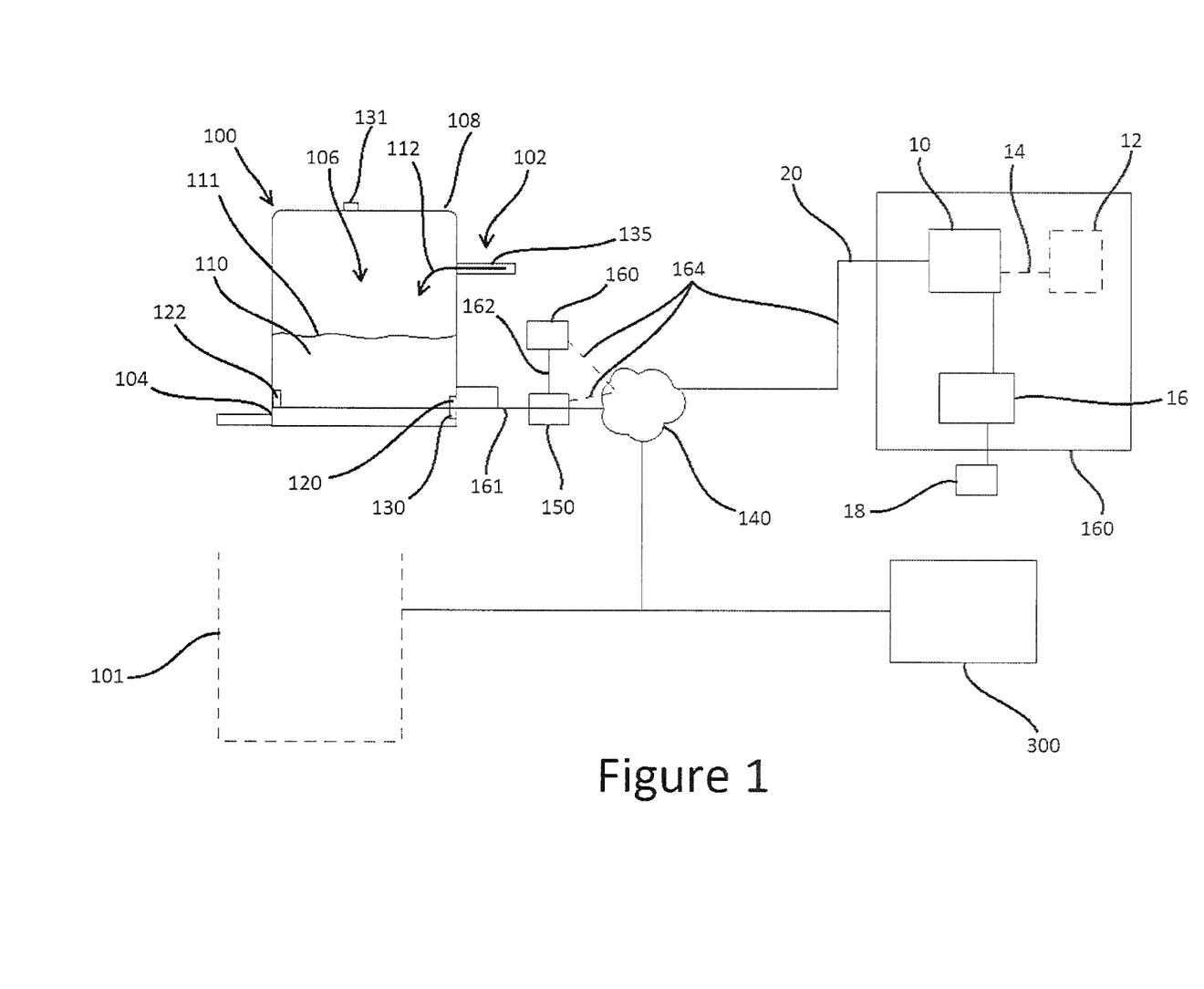
FIG. 1 is schematic representation of the bulk fluid monitoring system of the present invention.

In a preferred embodiment of the present invention, a bulk fluid monitoring system including a processor in the form of a monitor 10 is provided as shown in FIG. 1. A monitor 10 includes input 20 to provide information in relation to parameters of a fluid of a bulk fluid container such as a tank or, as shown, a vat 100. The vat 100 includes internal space 106 able to contain a volume of the fluid. The vat 100 is adapted to hold a fluid 110, such as milk. The vat 100 has attached to it at least one sensor 120. The sensor 120 may measure one of many properties of the fluid 110. In the embodiment shown in FIG. 1, the sensor is a temperature sensor 120 that is adapted to measure the temperatures of the fluid 110 through a range of possible temperatures for that fluid 110 in the applicable environment, such as milk obtained from recently milked livestock. The sensor 120 is one of a plurality of sensors 120,122,130,135. The sensors 120,122,130,135 include the temperature sensor 120 and a fluid level sensor 130. The vat 100 includes an inlet port 102 and an outlet port 104. Other sensors (not shown) may be provided that measure parameters such as flow rate, for example as fluid 110 travels through the inlet or outlet ports 102,104. The fluid 110 level 111 may be measured a number of ways, including by using a ultrasonic pulse sensor 131 installed in the upper lid or ceiling 108 of the tank or vat 100 to detect the level 111 of the fluid 110 or a submersible pressure sensor 130. In the present embodiment, fluid level 111 is measured by reference to a flow rate sensor 135. The flow rate measurements from sensor 135 are employed to indicate start or end times in the delivery process of the fluid 110 to the vat 100.

The flow rate sensor 135 is installed at or adjacent the inlet 102 and includes non-invasive or non-contacting pulse detection or infra-red techniques that measure flow rate without contaminating the fluid 110.

Figure 2:
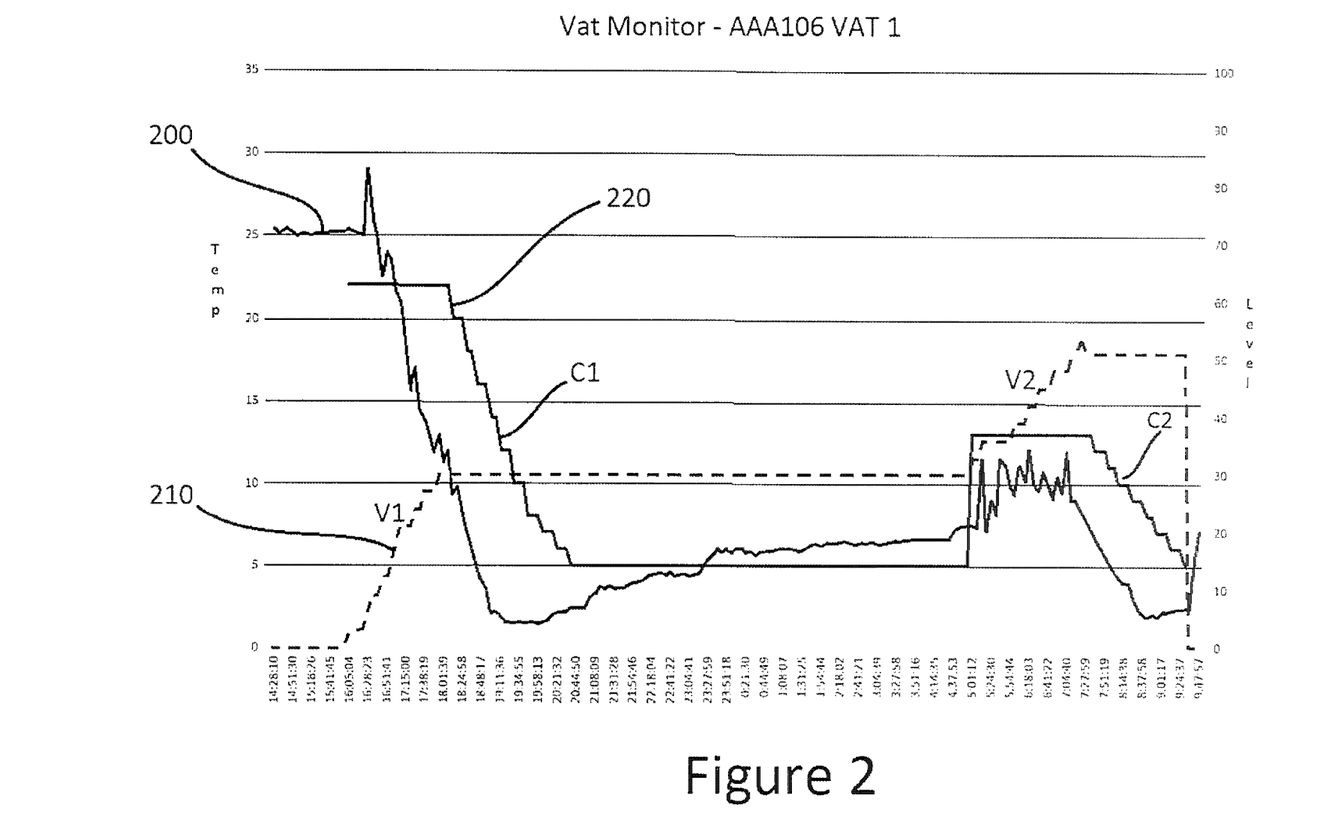
FIG. 2 is a graph representing an example of a temperature, volume and a milk cooling curve of a bulk fluid in accordance with the present invention.

The fluid 110 in the form of milk requires cooling as soon as it enters the internal space 106 of the vat 100 for storage. There may be multiple milkings that each deliver a batch of milk per vat to the vat 100 over a period of time. Each influx of milk from a new milking not only increases the volume $V_1$ of the fluid 110 in the vat 100, but also increases the temperature of the fluid 110 already contained in the vat 100. The milk 112 newly introduced to the vat 100 is warmer than the collected fluid 110 already in the vat internal space 106. The just-collected milk 112, typically may have a temperature of up to or around 37° C. The newly collected milk 112 mixes with the previously collected, and cooled, fluid 110. The previously stored fluid 110 is ideally stored at a target temperature T at or below a temperature according to a milk cooling curve. A cooling curve 220 suitable for the introduction of new milk 112 into the vat 100 is shown in FIG. 2. The target temperature T will vary depending on what is applicable for the particular application and jurisdiction. For example, a target temperature T in the range of 2-8° C., specifically such as 2, 4, 6 or 8° C., may be applicable. An example of temperature and volumes of fluid 110 in the vat 100 is shown in FIG. 2. The temperature sensor 120 measures the temperature of the fluid 110 in the vat 100 and outputs this data via a communication link 161. Temperature data from the temperature sensor 120 is shown in FIG. 2 as a temperature line 200. In terms of a time line, the corresponding information from volume sensor 130 is shown in the form of volume line 210. Using a 24 hour clock, the horizontal time line shown in the FIG. 2 graph spans a period from mid-afternoon (14:28 or 2.28 pm) to mid-morning (9:47 am) of the following day, i.e. a period of just over 19 hours.

In the FIG. 2 example shown, the vat 100 starts off empty with zero volume $V_1$ of fluid 110 at 15:41. When a new milking occurs, commencing at around 4 pm, the affect is to increase the volume V with an initial volume $V_1$ of milk in the vat 100 as new milk 112 is added to the initially empty vat 100. The volume line 210 is shown to rapidly increase over a period until about 6 pm from an initial zero base. When the new milking finishes delivery of new milk 112 at around 6 pm, the level 111 is just over 30% of the vat's 100 maximum volume capacity. During the first new milking period between about 4 and 6 pm, actively cooling of the vat's fluid 110 contents over a period of about 150 mins., from an initial temperature T spike of about 29° C. around 4.30 pm to about 2° C. at about 7 pm.

When an additional second or subsequent milking occurs in which a further batch of new milk 112 is delivered into the vat 100 having already received the first initial batch of fluid 110, the newly milked or obtained milk 112 is added to the existing stored fluid 110 in the vat 100. This is represented in the graph in FIG. 2, with the second batch of new milk 112 commencing to be delivered through the inlet 102 into the vat 100 at about 5 am on the timeline, with delivery to the vat 100 of a second batch volume $V_2$ of milk completed just after 7 am, i.e. over a second batch delivery period of about 2 hours.

The added milk 112 of volume $V_2$ from the second batch will have a higher temperature, compared to the ambient temperature, and compared to the already cooled fluid 110 in the vat 100. This causes an overall increase in the temperature of the fluid 110 in the vat 100, as well as an increase in the volume V of the mixture of milk fluid 110,112 in the vat 100 to just over 50% of the capacity of the vat 100 as represented by the volume line 210.

FIG. 2 shows a graphical representation of an example of a cooling curve 220. The target cooling curve 220 is shown as a comparison with the actual temperature line 200, allowing a visual representation of the actual temperature 200 of the milk 110 in the vat 100 compared to the permissible or desirable range of temperatures of the milk over time as represented by the cooling curve 220.

The monitor 10 compares the data from the temperature sensors 120 to the desired temperature of the fluid 110 as represented by the cooling curve 220.

In FIG. 2 the bottom axis represents time, from 14:28:10 to 9:47:57. At TIME 23:27:59, the temperature of the fluid 110 as represented by data from temperature sensor 120, has increased to a temperature beyond the maximum allowed, that is to a value above the cooling curve 220 desirable temperature range of no more than 5° C. This is represented by the temperature line 200 intersecting, and then rising above, the cooling curve 220. In one embodiment, a separate output may be generated to one or more destinations, including direct to a vat controller 150 or to an external controller resource 300. The vat controller 150 may receive raw data from the sensors 120,122,130,135 and a separate data 20 may be generated by the controller 150 or a remote server 160 and sent to the external controller resource 300.

Figure 3:
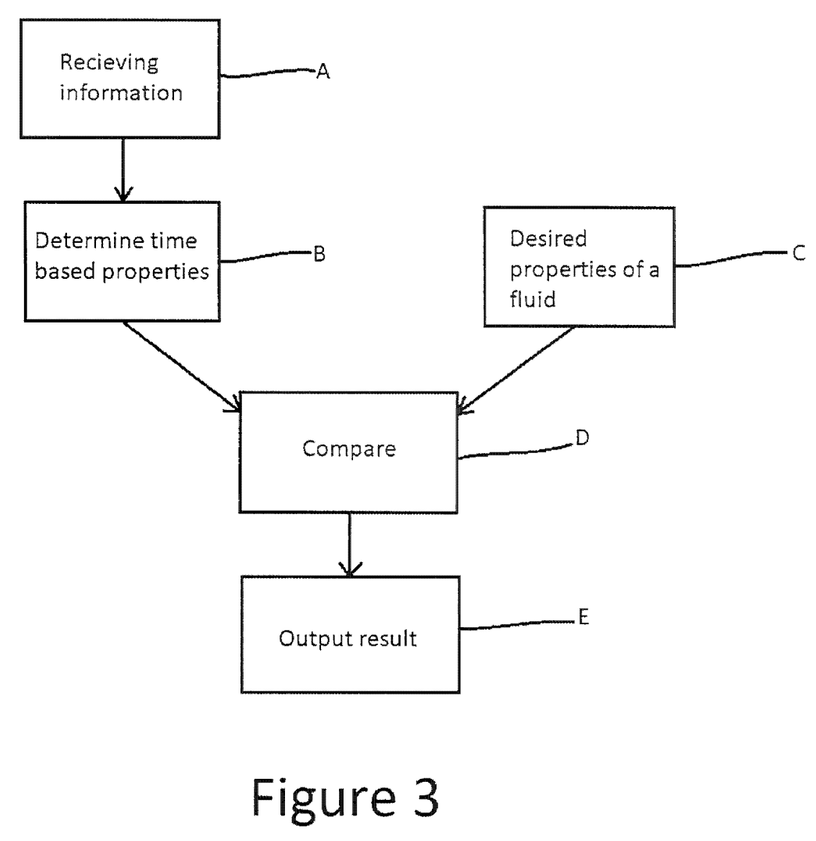
FIG. 3 is a flow chart of an example method for monitoring a bulk fluid in a container in accordance with the present invention.

Advantageously, the processor 10 is used to control the sensors and generate alerts. The evaluation ad action procedure followed by the processor monitor 10 is shown in FIG. 3 in which the monitor 10:

A. receives information from the sensors 120,122,130,135;
B. determines time based properties such as temperature per time associated with the milking event in which new milk 112 is delivered to the vat 100;
C. determines an appropriate cooling curve 220 or portion thereof that is applicable to the instance or operation associated with the milking event, using the appropriate curve to determine time based properties such as the desired temperature per time;
D. compares the real data of B with the target data of C; and
E. generates an output in the form of an alert if step indicates the information of B falls outside the parameters of C.;

The processor 10 is, in the embodiment shown, located remotely and adapted to receive and control the monitoring of a plurality of like milking operations at various scattered dairy installations. The processor 10 may generate the output 16 which in turn leads to the activation of an indicator 18. The indicator 18 is adapted to provide an audible or visual signal associated with the indicator 18 indicating that there is non-compliance in relation to one of the fluid property parameters. The indicator 18 may include a visual or audible indication of whether the properties of the bulk fluid 110 being monitored are within one of, or a plurality of, parameter standards, such as the cooling curve 220 for target temperature over time during delivery of first and second batch volumes $V_1, V_2$. The parameter standards are advantageously stored on one or more of the processor devices 10,150,160,300.

In the graph shown in FIG. 2, steep transitions such as that shown at lines C1,C2 (such as C1 for the cooling curve 220) indicate stepped transitions. The theoretical curve would be a generally smooth curve. However, the stepped curve 220 reflects a real world curve of the desirable cooling parameters applicable to the present embodiment. This reflects the periodic sampling of the milk fluid 110 temperature as the temperature measurements are incrementally taken over time.

Milking times may vary. This has led the Applicant to develop milk cooling curves or cooling envelopes which provide a predetermined time-and-temperature requirement for freshly obtained milk from multiple batches obtained from separate milking events. The milk cooling curve is effectively the upper limit of acceptability of temperature of the collected milk at a time from start or completion of a milking event.

Keeping the fluid 110 in the vat 100 at temperatures below the predetermined time and temperature requirement indicated by the cooling curve 220 provides confidence for the dairy suppliers that the fluid 110 is safe for consumers.

There is also the added complication that milk transporters may pick up the fluid 110 contained in the vat 100 at different times taken from either the start of milking or at the end of the milking event. For example, a tanker 70 may take delivery of the fluid 110 within 3.5 hours from first milking (about 4 pm in FIG. 2), or 2 hours from end of milking of the first batch $V_1$ (about 6 pm in FIG. 2), which may be before it is cooled to the desired temperature corresponding to the cooling curve recommended temperature at the time on the time line.

Ensuring the predetermined time-and-temperature requirements have been applied to the collected fluid 110 allows the vat 100 to contain the milk 110,112 from multiple milkings $V_1, V_2$, and to be transported prior to complete cooling, and still comply with standards.

To monitor temperatures of the fluid 110 in the vat 100, devices such as the Smarta Industrial SF104 Vat monitor sold by the Applicant may be used as the controller 10. This controller device 10 may be used to measure and communicate milk temperature, and to generate a response if parameters are exceeded and an alert is required.

The vat 100, in the present embodiment, is located remotely from the monitor 10, and data or information is communicated by any one or more of a number of suitable communication methods, including wired or wireless networks, such as mobile data networks, or satellite transmissions, and/or via the Internet.

FIG. 1 shows a connection via the internet 140 where a cloud-based solution is offered. The type of communication method chosen is dependent on the requirements of the dairy and milk processors, including the possibly remote and/or disparate dairies and the dairy processing and packaging installations, which may be more central or metro-located. The communication method may be two way. The communication method may allow information to be transmitted directly back to an individual vat controller 150 such as a Smarta sf104 sold by the Applicant.

The monitor 10 provides information back to the controller 150 to allow on-site monitoring of properties of the fluid 110 in the vat 100. This may be useful if there are potential issues with the operation of the vat 100. Problems may include the fluid 110 not being cooled sufficiently to comply with one or more desired time and temperature requirements. Another advantage is that the monitor 10 may be used to output the data to an external resource or entity 300. This may include, for example, third parties such as milk producers, which may use the data to schedule deliveries, and log the data on the handling of the milk from collection to delivery. This better ensures integrity and safety of the product to consumers.

Therefore, the vat 100 can have data logged in relation to its content (eg. fluid 110), and that data may be made available to third parties such as logistics companies which may use information derived from the data to pick up the fluid 110 from the vat 100 and to deliver it to milk processors. The milk processors may use the data to confirm (or establish the opposite) that the milk complies with an applicable cooling curve standard. The standard may involve, for example, temperature and time data contained in the milk curves. The data provided by the monitor 10 may be used to record the temperature of the fluid 110 over time when it was in the vat 100.

The monitor 10 may control the monitoring of more than the one vat 100 (additional vats 101 are represented in FIG. 1 by dotted lines). Each additional vat 101 may have the same equipment, such as ports 102,104 and sensors 120, 122,130,135 as the first vat 100. In such a scenario, each vat or group of vats 101 is individually identified, with data stored in relation to each vat or group of vats 101 with alerts 18 and curves 220 for each individual or group of vats 101. This will also be useful where an installation for extracting or obtaining the fluid 110, eg. a dairy farm, has more than one vat 101.

The temperature sensor 120 may include more than one temperature sensor, such that spaced sensors are located in different zones of the vat 100, or the inlet 102 or the outlet 104. The information from the temperature sensors 120,122, and/or the flow rate sensor 135 and/or the fluid level sensor 130, may be used to determine when the vat 100 is in use and when milking has commenced or completed.

For example, Food Standards Australia and New Zealand (FSANZ) guidelines for raw milk collection advise that milk should be cooled on farm to 5° C. within 3.5 hours from the start of milking. During milking, the temperature of the contents of the vat 100 will increase due to the milk being around 37 degrees when taken from animals.

As the new milk 112 flows to the vat 100, the level sensor 130 will indicate an increase in volume of the fluid 110 in the vat 100. The inflow of new of milk 112 will also result in an increase in the temperature of the fluid 110 in the vat 100, which is detected by temperature sensor 120 and/or temperature sensor 122. This is communicated to monitor 10.

The monitor 10 can determine the time that milking has started using this information and match it to the applicable standard milk cooling curve to determine whether the milk is being subjected to a rate of cooling that is within the cooling curve parameters and is otherwise handled appropriately. The monitor 10 may be used to schedule a pick up of the milk for delivery to a producer, or a milk processing and packaging installation. The producer may be permitted and equipped to remotely access the data and information supplied by the monitor 10 to schedule a pick-up and delivery, whilst also confirming compliance with the applicable standard(s). The memory of the monitor 10 can store the data to provide a history of the milk fluid 110,112. The producer may store the corresponding data for compliance and auditing purposes.

In comparison, European food standards for milk are based on the time that the milking is completed. The monitor 10 may use information from the fluid level sensor 130, and optionally may also use information from either or both of the temperature sensor(s) 120,122, or the flow rate sensor 135, to determine the end of a milking session. When milking finishes, the volume no longer increases, but stays static (as measured by the fluid level sensor 130), flow ceases (as measured by the flow rate sensor 135), or the temperature drops at a characteristic rate in that the temperature of the milk starts to decline due to the cooling provided by the vat 100 (as measured by either or all of the temperature sensors 120,122). From this information sent to the monitor 10, the monitor 10 can determine whether the milk fluid 110,112 is in compliance with the applicable standard, such as in Europe, in respect of which cooling is required based on the time milking is completed. Further, the monitor 10 may compare the data on the milk 110 in the vat 100 to determine whether it complies with both FSANZ and European standards.

The monitor 10 may store test criteria corresponding to one or more milk cooling curves (such as curve 220 or the FSANZ standard). The monitor 10 can store a number of cooling curves, including the FSANZ and European standards. The monitor 10 allows additional custom cooling curves to be input, installed or loaded or stored on the monitor 10. The monitor 10 can compare the information from the sensors 120 or 130, and/or additional sensors 122,135, said information being logged either on the monitor 10 or separately, for example on a separate memory or storage device 12, in data transfer communication with the monitor/processor 10 by either cable or wireless connection 14. Information from sensors 120, 122, 130 and 135, can be transmitted in real time to the monitor 10, or can be stored and compared. The information may be released to an interested party upon request of, for example, a milk producer, processor or logistics company.

The vat controller 150 can have additional inputs. These include connections to other electrical equipment, such as computer processors which schedule milking time starts. The other electrical equipment may be activated during milking to provide additional information on milking time starts and/or completion.

The monitor 10 can utilise software run on the remote server 160 as shown in FIG. 1. The communication connection is a direct cable or wireless connection 162, such as via a LAN modem, or may use an internet communication protocol 164 via the World Wide Web (www). The server 160 can run a number of other programs and have functions for input 20 and output 16 of data, and storage in the memory 12 of information from the sensors 120 or 130 or additional sensors, such as sensors 122,135. The monitor 10 has access to memory 12 to store information from the sensors such as sensor 120,122,130 and 135, and also has a processor to process information.

The monitor 10 can run one instance or operation for each vat 100. However, it is capable of receiving data from a number of vats 101, wherein said data from each vat 101 is managed, monitored, stored and reported separately.

The monitor 10 includes software that runs on dedicated hardware. The software can be designed to be specific to one vat 100 or to a group of vats 101. In the example, all of the vats 101 are located at one dairy or installation. In this case, the monitor 10 is located at the installation and is responsible for communication with external entities, such as logistics companies, producers, managers or milk processors, via standard communications methods, such as the Internet, mobile communications network, wireless networks or landline telephone networks.

Figure 4:
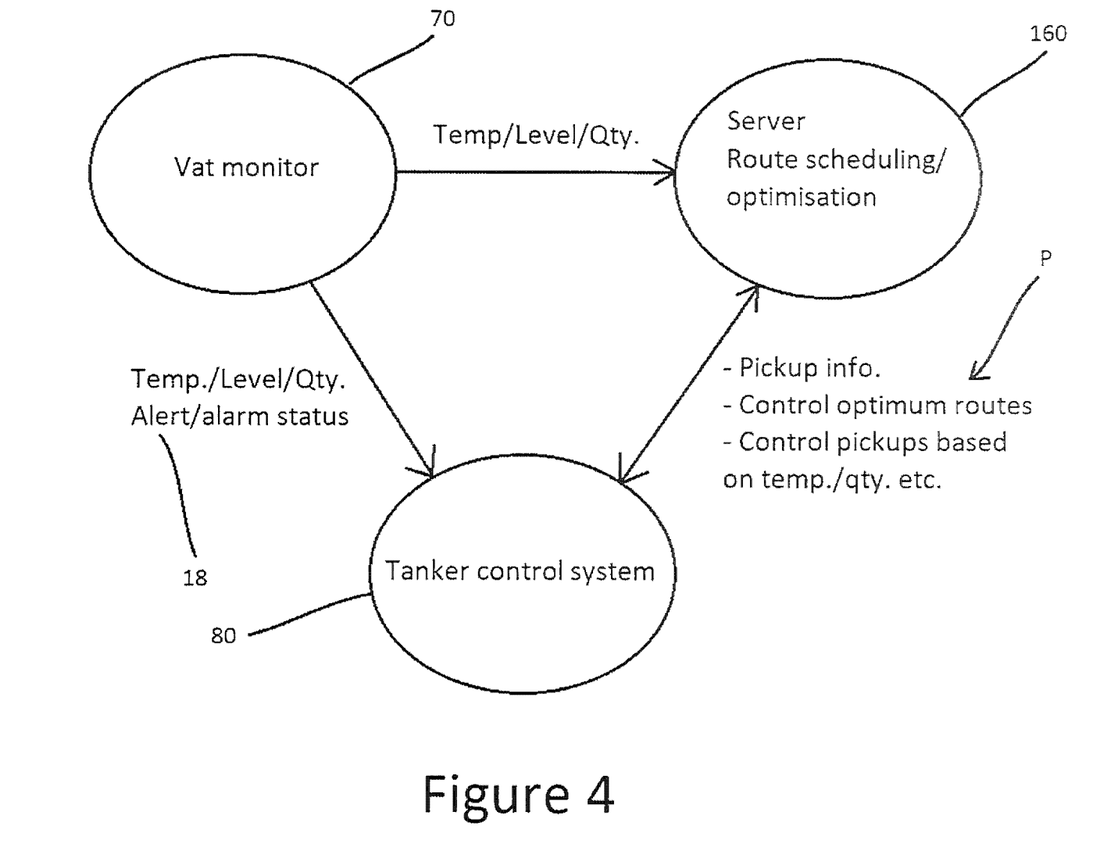
FIG. 4 is a flow chart of an example method for monitoring a bulk fluid in a container in accordance with another aspect of the present invention.

In another aspect of the invention, FIG. 4 represents the activities and information flow in relation to the monitoring system and the tanker control system. The vat 100 control system described with reference to FIGS. 1-3 is combined to accurately plan routes for at least one tanker 70. This ensures that the bulk fluid 110 pickups are done in the most efficient manner to reduce the tanker's 70 mileage and transport time. It may also protect and guarantee that bulk fluid 110 quality complies with the standard.

Figure 5:
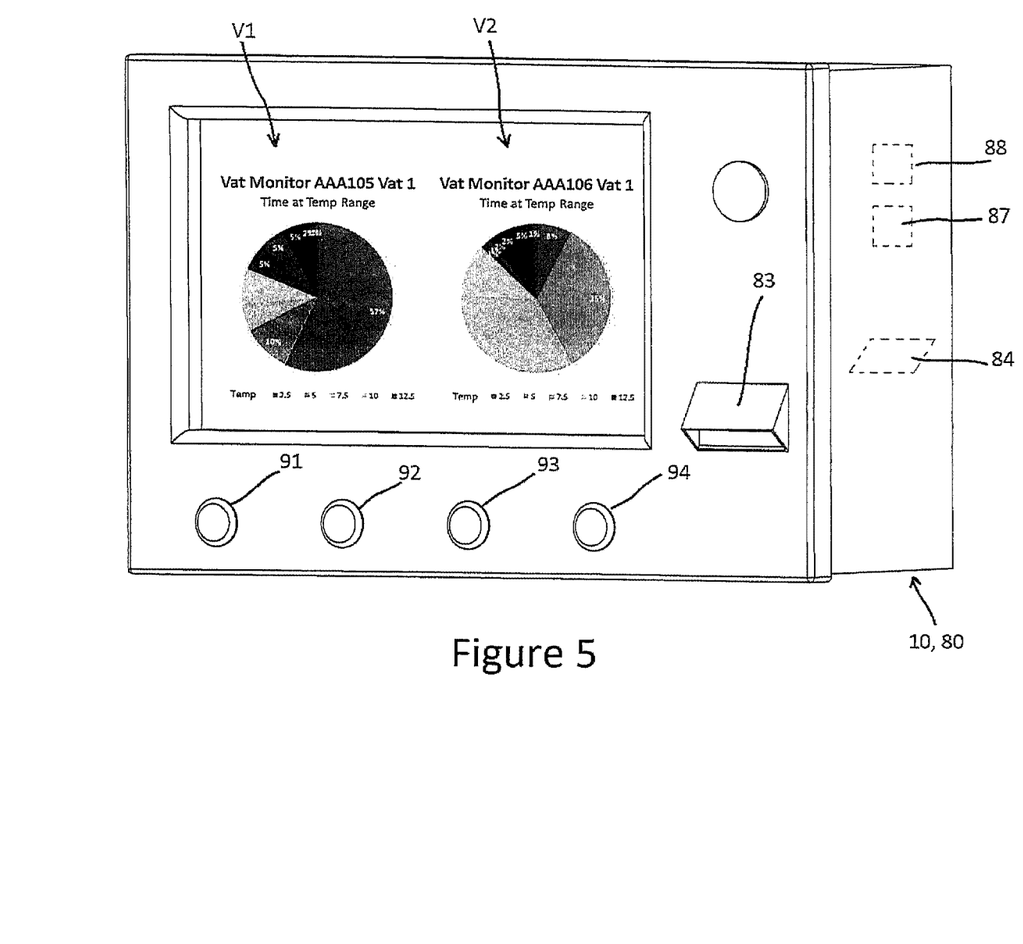
FIG. 5 is a perspective view of a monitor/processor module for use with a system according to one aspect of the invention.
Figure 6:
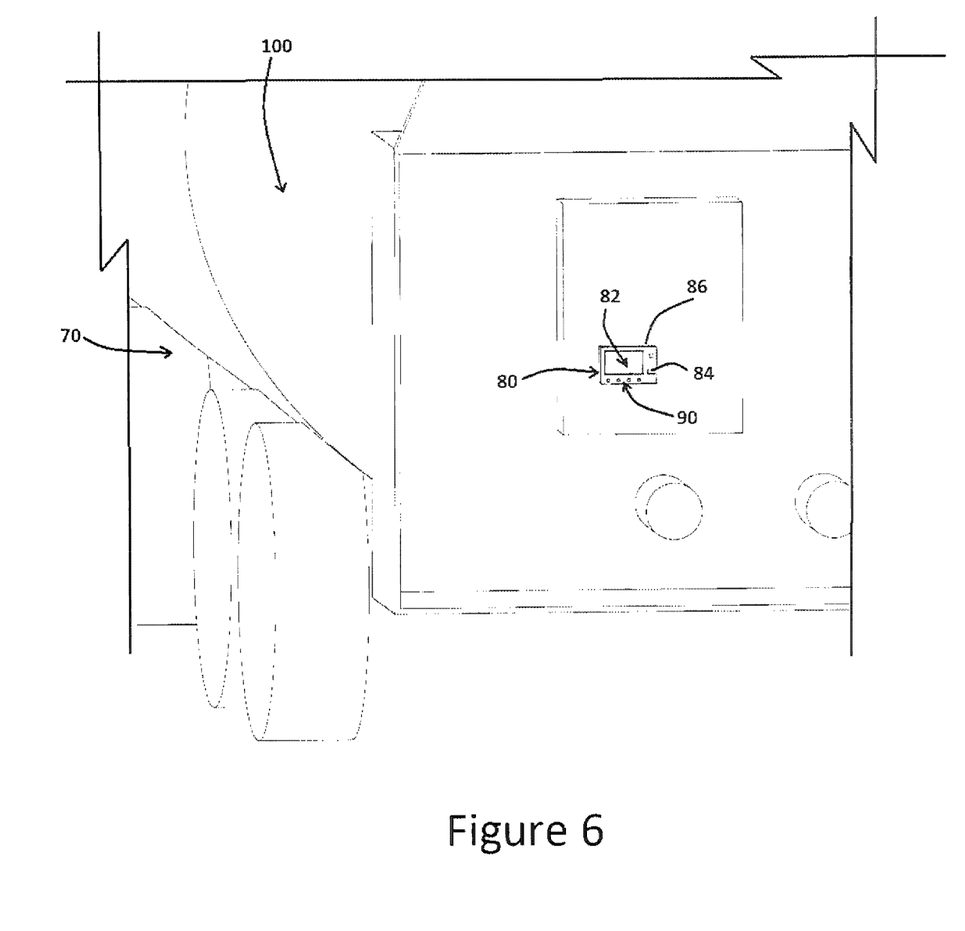
FIG. 6 is a perspective rear view of a tanker transport having installed therein and thereon a system according to one aspect of the invention.

The monitor 10 is shown in FIG. 5. The monitor 10 may be adapted for use as a controller 80 for use on a tanker vehicle 70 as shown in FIG. 6. It is preferred for quality assurance purposes that the monitor 80 is approved by the National Measurement Institute Australia (NMI) for use in vehicle-mounted milk metering applications. The monitor 10 is ideally designed to be retro-fitted to existing dairy installations with approval for use with all existing common flowmeters 135. The device 10 should have a rugged build, preferably using stainless steel and marine grade alloy materials to ensure reliability, weather-resistance and durability. The monitor 10 shown has a 10 inch (250 mm) touch display screen 82 that allows ease of use, even in dim lighting conditions.

The batch volumes $V_1, V_2$, are displayed on the screen and show an operator the breakdown of time that each batch $V_1, V_2$ spent at key temperature markers 2.5, 5, 7.5, 10 and 12.5° C. in terms of the percentage of total time in the vat 100. The earlier batch $V_1$ had a longer time to cool in the vat 100 and therefore With reference to FIG. 7, the monitor 10 performs a full functional self-check on initialization to ensure that all attached devices, including flow meters 135, temperature sensors 120, or valve controlling solenoids 13 are operating and within specifications. This ensures that the operator or tanker driver will not get to a pickup only to realize there is a fault in the system 1, such as a faulty solenoid.

The monitor 10 allows a user to log in to the system 1 with a barcode 83 or RFID scan using a scanner 84. By uploading data specific to the user and their corresponding installation(s) and/or vehicle, the scanning function 84 facilitates auto loading of a calculated and allocated route. This is uploaded from the monitor 10 to the server 160.

The monitor 10 is coupled to the cloud-based platform loaded on the server 160 to provide a scalable solution that is accessible from any internet connected device. The platform is preferably hosted in a Virtual Private Cloud computing environment in a remote data center with separate geolocation of backups to ensure:

security of data;
continuous system availability and reliability; and
simple web browser access to a cloud-based portal.

Figure 7:
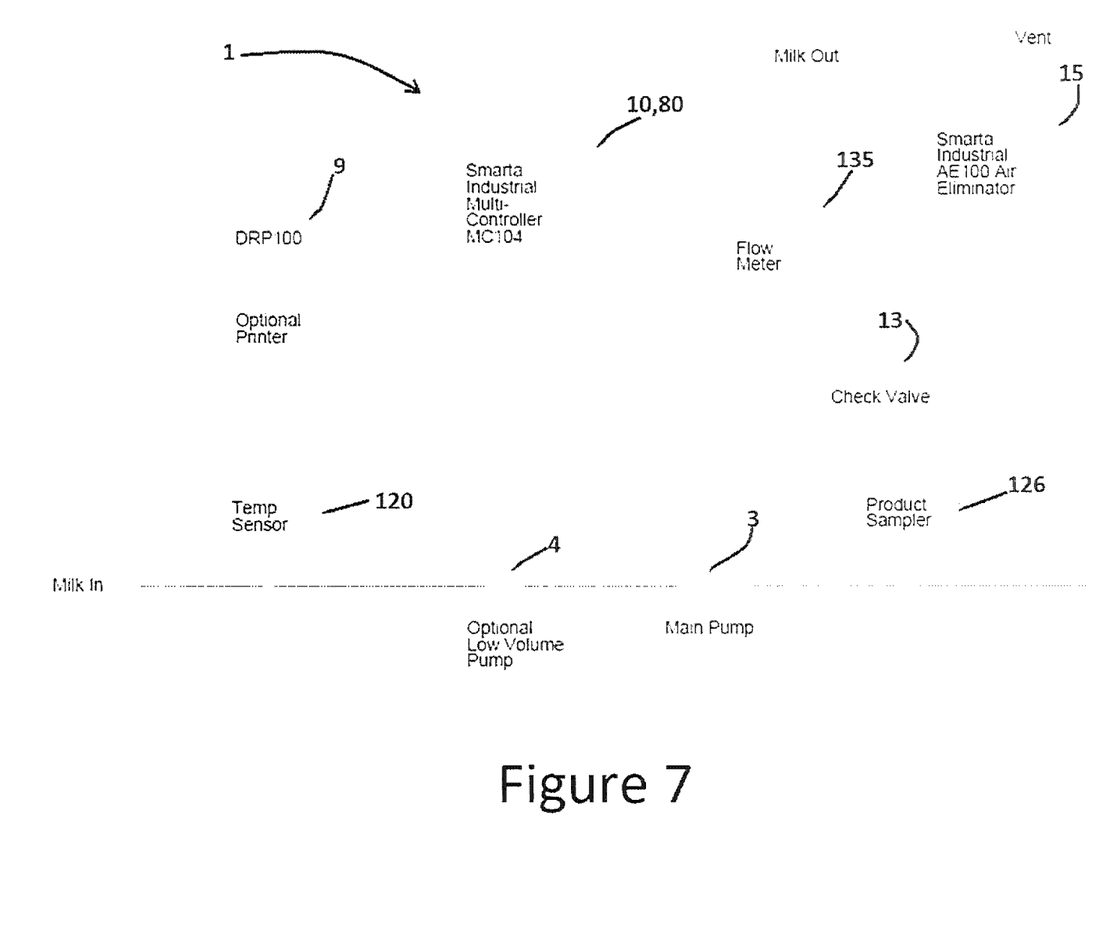
FIG. 7 is workflow chart for a system according to one aspect of the invention.
Figure 8:
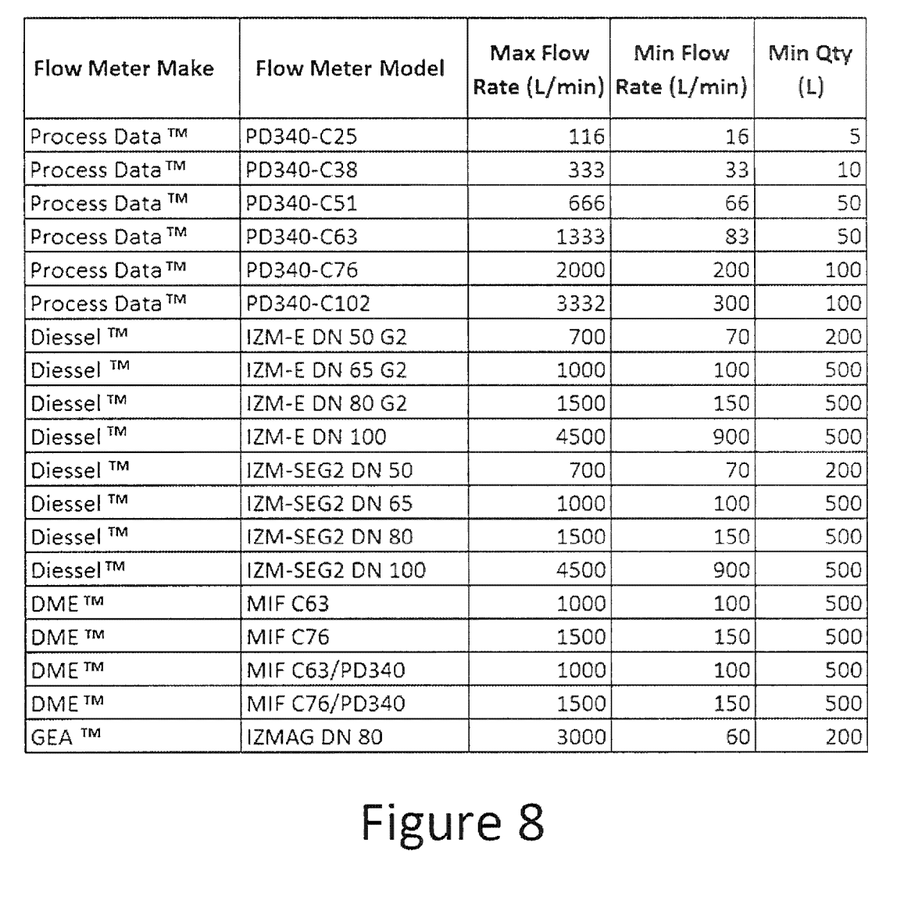
FIG. 8 is a table of alternative maximum and minimum flow rates for use in a flow meter incorporated in a system made according to one aspect of the invention.

The solution provided by the system 1 of the invention means that end users are not required to own and maintain their own application servers, networks and connections. FIGS. 6 and 7 show the monitor in the form of a controller 80 that is setup for the vehicle 70. The controller 80 acts as a mounted milk meter application that operates in the system 1 comprising the following components:

the functionality of the monitor 10 in the form of a multi controller-tanker monitor or processor 80;
a high volume pump 3;
an optional low volume pump 4;
an air eliminator device 5 in communication with a vent;
a flow meter 135, (the specifications of which are detailed in the table provided in FIG. 8 in which a variety of suitable milk flow meters by make and model are shown with regard to their flow rate and volume ranges of operation. The flow meter 135 can be used to estimate accurately the volume V in the vat or tank 100);
a temperature sensor 120;
a product sampler 126; and
an output device 18 in the form of a docket and label printer 9.

Referring to FIGS. 5-7, the multiple tank controller 80 is a fully integrated control unit specifically designed for use as a vehicle-mounted milk metering and monitoring application. The controller 80 is loaded with a dedicated SmartaTrans 1.x version of software available from the Applicant.

The monitor or controller 10,80 has the following features:

full stainless steel and marine grade alloy sealed enclosure 86 designed with multiple mounting points for ease of installation on the vehicle 70;
10 inch (250 mm) display and touchscreen 82 that provides easy to read display and fully functional touchscreen menus and keyboards for easy use;
operator control buttons or knobs 90, which may be in the form of 4 LED back-lit stainless steel buttons that perform to allow the user to select full normal pickup 91, route 92, delivery 93, and CIP (Cleaned in Place) 94 operational functions;
RFID reader 84 for user/driver login/device access;

2 dimensional barcode reader 83 to read normal barcodes and QR codes to allow user access functions, settings autoload, route number/detail autoload, and/or factory specific number autoload. This may reduce the need for any manual entry of information into the monitor or controller 10,80 by the user and may eliminate manual data entry mistakes;

inbuilt 3G/4G modem 87 that allows the device to connect to the server 160 to get data including users, routes, suppliers, factories etc and upload route, pickups, CIP, and unload data;

inbuilt GPS unit 88 to allow the device to confirm a current pickup of, for example, batch volumes $V_1, V_2$, by the supplier pre-loaded geo-location data and real-time tracking of devices and transport 70;

built to allow for multiple pumps 3,4, multiple temp sensors 120,122, multiple samplers 6, control of up to 24 solenoids 8,126 and receive up to 12 digital and analogue inputs 20;

connects to docket printer 9 that prints full size 80 mm docket labels, including logos, barcodes and QR codes—and prints 60 mm labels with text, logos, barcodes, and QR codes;

programmed to allow for routes, pickups, CIP, factory numbers, multiple samples, sample flushing/cleaning, multiple vats, trans-ship function; and/or programmed to enable calibration self-calculation with certified electronic sealing that allows setting up or calibration by an operator's appropriate selection of the LED buttons 90.

The coupled monitoring and controller systems shown in FIGS. 1 and 7 with reference to monitor 10 and controller 80 can combine to generate a dynamic route scheduling system 1 that secures timely tanker 70 pickups and unloading to ensure food safety standards are adhered to from milking to delivery to the producer or other end destination. As shown in the FIG. 4 flow diagram, the monitor 10 interprets the sensor 120,122,130,135 data over time and communicates critical temperature T, level 111, volume V information to the controller 80, generating an alert or alarm 18 for an operator if required parameters are not met. The monitor 10 communicates to the server 160 the critical information T, 111, V for the server to determine optimal tanker 70 route scheduling, the server 160 in turn communicating to the controller 80 of each tanker 70 the pickup and delivery information P, based on the critical status of the fluid 110 in each batch volume V in each tank or vat 100. Throughout the specification and claims the word "comprise" and its derivatives are intended to have an inclusive rather than exclusive meaning unless the contrary is expressly stated or the context requires otherwise. That is, the word "comprise" and its derivatives will be taken to indicate the inclusion of not only the listed components, steps or features that it directly references, but also other components, steps or features not specifically listed, unless the contrary is expressly stated or the context requires otherwise.

In the present specification, terms such as "apparatus", "means", "device" and "member" may refer to singular or plural items and are terms intended to refer to a set of properties, functions or characteristics performed by one or more items or components having one or more parts. It is envisaged that where an "apparatus", "means", "device" or "member" or similar term is described as being a unitary object, then a functionally equivalent object having multiple components is considered to fall within the scope of the term, and similarly, where an "apparatus", "assembly", "means", "device" or "member" is described as having multiple components, a functionally equivalent but unitary object is also considered to fall within the scope of the term, unless the contrary is expressly stated or the context requires otherwise.

Orientational terms used in the specification and claims such as vertical, horizontal, top, bottom, upper and lower are to be interpreted as relational and are based on the premise that the component, item, article, apparatus, device or instrument will usually be considered in a particular orientation, such as with the vat 100 upright. It will be appreciated by those skilled in the art that many modifications and variations may be made to the methods of the invention described herein without departing from the spirit and scope of the invention.

The invention claimed is:

1. A bulk fluid monitoring system for measuring actual time critical properties of a bulk fluid delivered to a storage container and comparing the actual time critical properties to a standard, the system including:
    a plurality of sensors that provide sensor data in relation to measurements of a plurality of the actual time critical properties of the bulk fluid;
    a memory holding:
        a set of the sensor data of the actual time critical properties provided by the plurality of sensors; and
        a predetermined set of data parameters that comply by falling on or within ranges of values either side of a standard curve representing at least one of the time critical properties for the bulk fluid; and
    a processor suitable to:
        process the sensor data to generate sensor information;
        compare the sensor information with the set of data parameters to generate a compliance value; and
        send a signal to an output to generate an indicator of non-compliance where the compliance value corresponds to one of the actual time critical properties of the bulk fluid being outside the set of data parameters
    wherein:
    the actual time critical properties are in the form of a temperature of the bulk fluid over time and a change in the volume of the bulk fluid over time;
    the plurality of sensors include a sensor for measuring the temperature of the bulk fluid over time and a sensor for measuring the change in volume of the bulk fluid over time;
    the measurements are progressively recorded in the memory as the bulk fluid is collected and delivered to the storage container;
    the set of data parameters includes a time critical bulk fluid property vital for food safety and the processor stores the set of data parameters as a standard adapted to be graphically represented as the standard curve; and
    the change in volume of the bulk fluid corresponds to a fluid collection event in which new fluid is delivered to the storage container, the measurement of the change in the volume of the bulk fluid enabling the processor to determine the time that collection of the fluid started and the time of completion of collection of the bulk fluid for each separate fluid collection event.

2. The bulk fluid monitoring system of claim 1, wherein the output provides information to one or more of:
    a data logging device;
    a communication network to transmit information to a remote location;
    an indicator.

3. The bulk fluid monitoring system of claim 2, wherein the indicator includes a visual or audible indication of whether the properties of the bulk fluid being monitored are within the standards for temperature parameters stored on the device.

4. The bulk fluid monitoring system of claim 1, wherein the standard curve is a cooling curve that represents the maximum permissible temperature value of the bulk fluid at any one time over a specified period.

5. The bulk fluid monitoring system of claim 1, wherein the compliance value is represented in a fluid volume, viability and readiness indicator in the output device.

6. The bulk fluid monitoring system of claim 1, further including a tanker metering controller installed or mounted on a tanker vehicle.

7. The bulk fluid monitoring system of claim 6, wherein the controller is in communication with the monitoring device associated with the vat that is adapted to receive the bulk volume of fluid.

8. The bulk fluid monitoring system of claim 7, wherein the tanker vehicle has sensors for measuring at least the temperature of the bulk fluid contained in the vehicle tank over time.

9. The bulk fluid monitoring system of claim 6, wherein the tanker data measurements are collected by the controller and communicated to a remote server, the server processes the data from the processor relating to the comparison between the sensor information and the standard curve and the data from the controller relating to the vehicle's location and calculates an optimal driving route of the tanker vehicle for pickup and delivery time of the bulk fluid.

10. The bulk fluid monitoring system of claim 6, wherein the system includes multiple fluid volume, viability and readiness indicators each generated by one of a plurality of tanker metering controllers in spaced locations to prepare a transport schedule for a corresponding multiple of tanker vehicles.

11. The bulk fluid monitoring system of claim 6, wherein the curve is a stepped curve giving maximum permissible incrementally changing values sampled periodically.

12. The bulk fluid monitoring system of claim 6, wherein the curve is created by actual measurements of the time critical bulk fluid property taken over time using sensors in a vat adapted to perform like the sensors.

13. The bulk fluid monitoring system as claimed in claim 1, wherein the bulk fluid monitoring system further includes a tanker metering controller installed or mounted on a tanker vehicle.

14. The bulk fluid monitoring system as claimed in claim 1, wherein the bulk fluid is milk and system generates a time and temperature curve for the fluid including at least one milk cooling curve for the measured values of temperature and volume of the milk, the sensors adapted to progressively record the measured values as the bulk fluid is collected and delivered to the storage container, the measurements taken of the bulk fluid in the storage container as the volume of the bulk fluid in the storage container changes.

15. The bulk fluid monitoring system as claimed in claim 1, wherein the memory is in the form of a data storage device and the cooling curve is logged and stored in the memory to provide a full history of the temperature of the milk from initial collection in the storage container, to transfer to a tanker transport for delivery.

16. The bulk fluid monitoring system as claimed in claim 15, wherein the system provides a graphical representation of the cooling curve allowing a visual representation of the actual temperature of the milk over time in the storage tanker compared to a permissible or desirable range of temperatures of the milk over time as represented by the standard curve.

17. A bulk milk monitoring system for measuring actual time critical properties of milk delivered to a vat or tanker and comparing the actual time critical properties to a standard, the system including:
   a plurality of sensors that provide sensor data in relation to measurements of a plurality of the actual time critical properties of the milk;
   a memory holding:
      a set of the sensor data of the actual time critical properties provided by the plurality of sensors; and
      a predetermined set of data parameters that comply by falling on or within ranges of values either side of a standard milk cooling curve representing one of the time critical properties for the milk; and
   a processor suitable to:
      process the sensor data to generate sensor information;
      compare the sensor information with the set of data parameters to generate a compliance value; and
      send a signal to an output to generate an indicator of non-compliance where the compliance value corresponds to one of the actual time critical properties of the milk being outside the set of data parameters,
   wherein:
   the actual time critical properties are in the form of a temperature of the milk over time and a change in the volume of the milk over time;
   the plurality of sensors include a sensor for measuring the temperature of the milk over time and a sensor for measuring the change in volume of a volume of the milk over time;
   the measurements are progressively recorded in the memory as the milk is collected and delivered to the vat or tanker;
   the set of data parameters includes a time critical food safety property and the processor stores the set of data parameters as a standard adapted to be graphically represented as the standard curve; and
   the change in volume of the milk corresponds to a milk collection event in which new milk is delivered to the vat or tanker, the measurement of the change in the volume of the milk in the vat or tanker enabling the processor to determine the time that collection of the milk started and the time of completion of collection of the milk for each separate milk collection event.

18. The bulk fluid monitoring system as claimed in claim 17, wherein the milk is first collected in a bulk storage installation at the site of collection, the change in volume in the vat or tanker enabling the detection of the start, the filling period and the finishing time of the milking period, to provide the data required for a cooling curve for the milk in the vat or tanker.

* * * * *